US012788945B2

(12) United States Patent
Glandon et al.

(10) Patent No.: US 12,788,945 B2
(45) Date of Patent: Nov. 10, 2026

(54) CATHETER WITH ADVANCED LOCKING HUB FEATURES

(71) Applicant: Cook Medical Technologies LLC, Bloomington, IN (US)

(72) Inventors: Ronald Glandon, Chesterfield, MO (US); Gregory A. Frankland, Bloomington, IN (US); Patrick B. Snowhill, Bayville, NJ (US)

(73) Assignee: Cook Medical Technologies LLC, Bloomington, IN (US)

( * ) Notice: Subject to any disclaimer, the term of this patent is extended or adjusted under 35 U.S.C. 154(b) by 367 days.

(21) Appl. No.: 17/522,991

(22) Filed: Nov. 10, 2021

(65) Prior Publication Data

US 2022/0143365 A1 May 12, 2022

Related U.S. Application Data

(60) Provisional application No. 63/111,971, filed on Nov. 10, 2020.

(51) Int. Cl.
*A61M 25/00* (2006.01)
*A61M 25/01* (2006.01)
(Continued)

(52) U.S. Cl.
CPC .... *A61M 25/0097* (2013.01); *A61M 25/0074* (2013.01); *A61M 25/04* (2013.01); (Continued)

(58) Field of Classification Search
CPC .......... A61M 25/0097; A61M 25/0074; A61M 25/04; A61M 27/00; A61M 25/0017; A61M 25/0147
See application file for complete search history.

(56) References Cited

U.S. PATENT DOCUMENTS 5,522,400 A * 6/1996 Williams .............. A61M 25/04 600/585
6,673,060 B1 1/2004 Fleming, III
(Continued)

FOREIGN PATENT DOCUMENTS

EP 3 205 368 A1 8/2017
EP 3 205 369 A1 8/2017

*Primary Examiner* — Rebecca E Eisenberg
*Assistant Examiner* — Kate Elizabeth Strachan
(74) *Attorney, Agent, or Firm* — Woodard, Emhardt, Henry, Reeves & Wagner, LLP

(57) ABSTRACT

Described are catheters having a distal catheter tube region that can be secured in an anchoring profile by a locking engagement of a filament at a catheter hub. The catheter hub can include a locking arm that cooperates with a hub body to provide a locked position that compresses and positionally fixes a portion of the filament between a fixing surface of the locking arm and a fixing surface of the hub body. The locking arm can define a cutting notch in its outer surface through which a further portion of the filament passes in the locked position, and the further portion of the filament can be cut to release the secured condition of the anchoring profile as the locked position of the hub is maintained. The locked position defined between the hub body and the locking arm can leave at least portions of the respective fixing surfaces of the locking arm and the hub body spaced from one another a distance, when in a relaxed or unstressed condition. The locking arm can include first, second and third holes for routing the filament between the inner and outer surfaces of the locking arm, which can provide a filament path extending through the cutting notch and between the fixing surfaces of the locking arm and hub body. The locking arm can define a cinching notch for cinching and thereby securing a proximal-most segment of the filament.

26 Claims, 7 Drawing Sheets

(51) Int. Cl.
*A61M 25/04* (2006.01)
*A61M 27/00* (2006.01)

(52) U.S. Cl.
CPC ......... *A61M 27/00* (2013.01); *A61M 25/0017* (2013.01); *A61M 25/0147* (2013.01)

(56) References Cited

U.S. PATENT DOCUMENTS

| | | | | |
|---|---|---|---|---|
| 7,192,415 | B2 * | 3/2007 | Sauvageau | A61M 25/0147 604/95.04 |
| 7,217,256 | B2 | 5/2007 | Di Palma | |
| 8,177,773 | B2 | 5/2012 | Ovcharchyn et al. | |
| 2005/0203485 | A1 | 9/2005 | Lee | |
| 2006/0217667 | A1 | 9/2006 | Accisano, III et al. | |
| 2007/0032779 | A1 | 2/2007 | Accisano, III et al. | |
| 2007/0083189 | A1 | 4/2007 | Lampropoulos et al. | |
| 2009/0247990 | A1 * | 10/2009 | Ovcharchyn | A61B 17/0483 604/533 |
| 2011/0054447 | A1 | 3/2011 | Johnson et al. | |
| 2011/0295237 | A1 | 12/2011 | Eells et al. | |
| 2011/0313403 | A1 | 12/2011 | Hruska et al. | |
| 2013/0103004 | A1 | 4/2013 | Gray et al. | |
| 2014/0276655 | A1 * | 9/2014 | Murray | A61M 25/0147 604/540 |
| 2016/0228682 | A1 | 8/2016 | Graham et al. | |
| 2017/0056067 | A1 * | 3/2017 | Herscu | A61M 25/0017 |
| 2017/0232230 | A1 | 8/2017 | Valaie et al. | |
| 2017/0232231 | A1 | 8/2017 | Neoh et al. | |
| 2020/0164177 | A1 * | 5/2020 | Neoh | A61M 25/09 |

* cited by examiner

CATHETER WITH ADVANCED LOCKING HUB FEATURES

REFERENCE TO RELATED APPLICATION

This application claims the benefit of U.S. Provisional Application No. 63/111,971, filed Nov. 10, 2020 which is hereby incorporated by reference.

BACKGROUND

The present disclosure relates generally to medical catheters, and in particular aspects to catheters having hubs that cooperate with and grip a filament that secures the distal region of the catheter in an anchoring profile.

Catheters are used in a variety of medical procedures, including various drainage procedures such as drainage of the bladder, kidney or biliary system, abscesses, other sites of fluid collection. Typical drainage catheters have an externally-communicating filament lumen in their hub with a seal element (e.g. made of silicone) positioned in the filament lumen that seals around the filament to inhibit leakage of fluids through the filament lumen. Such catheters can also have features for gripping a length of the filament in order to secure the distal end of the catheter in an anchoring profile such as a coiled or "pigtail" profile.

There remain needs for catheters and methods for their preparation and use that effectively seal around a filament, manage proximal portions of the filament, and are robust in use, providing opportunities for multiple modes of operation in and around the catheter hub. Aspects of the present disclosure are addressed to these needs.

SUMMARY

Figure 1:
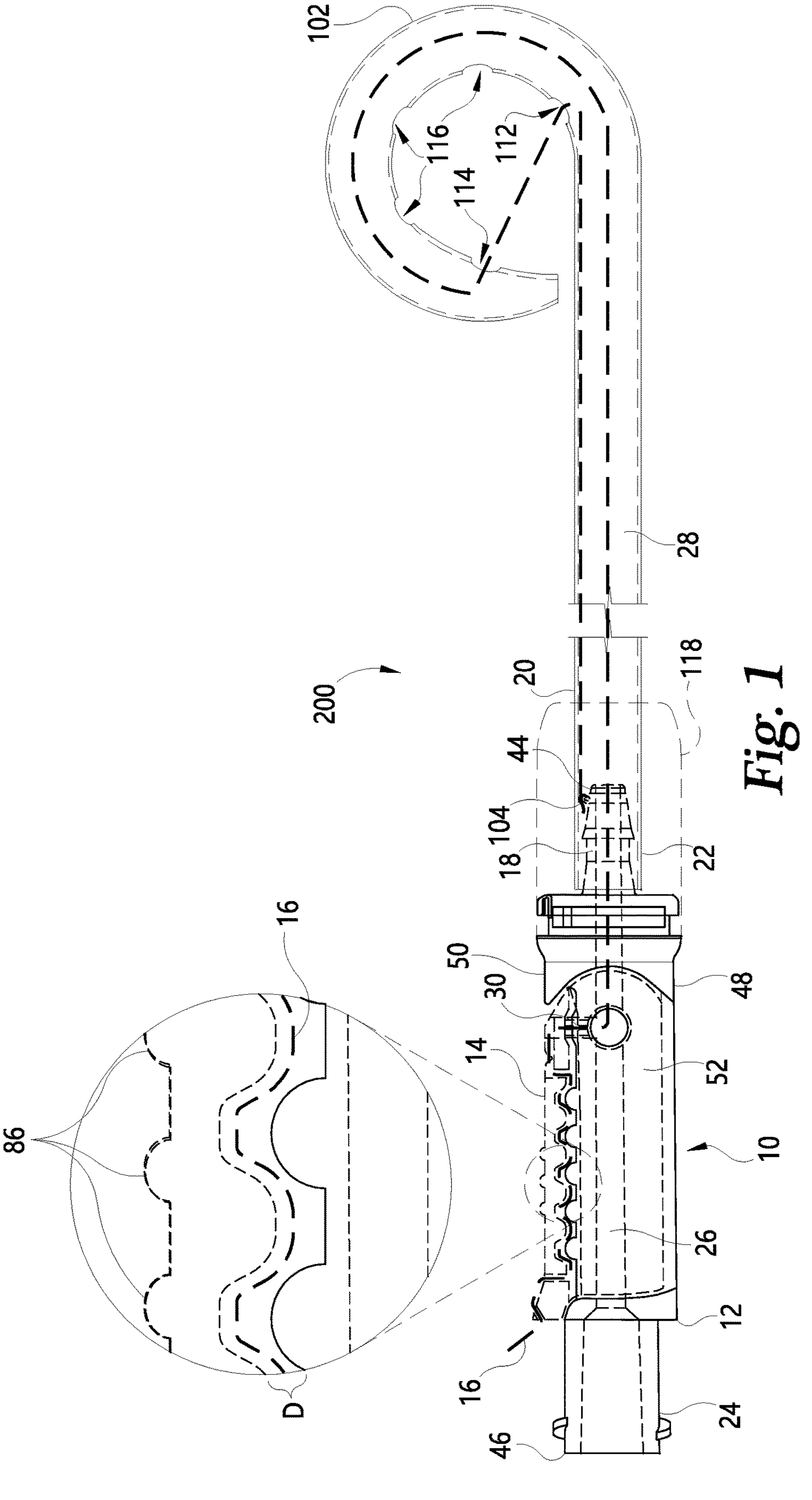
FIG. 1 provides an orthographic view of one embodiment of a catheter of the present disclosure, with some components shown in phantom to better illustrate internal features.
Figure 2:
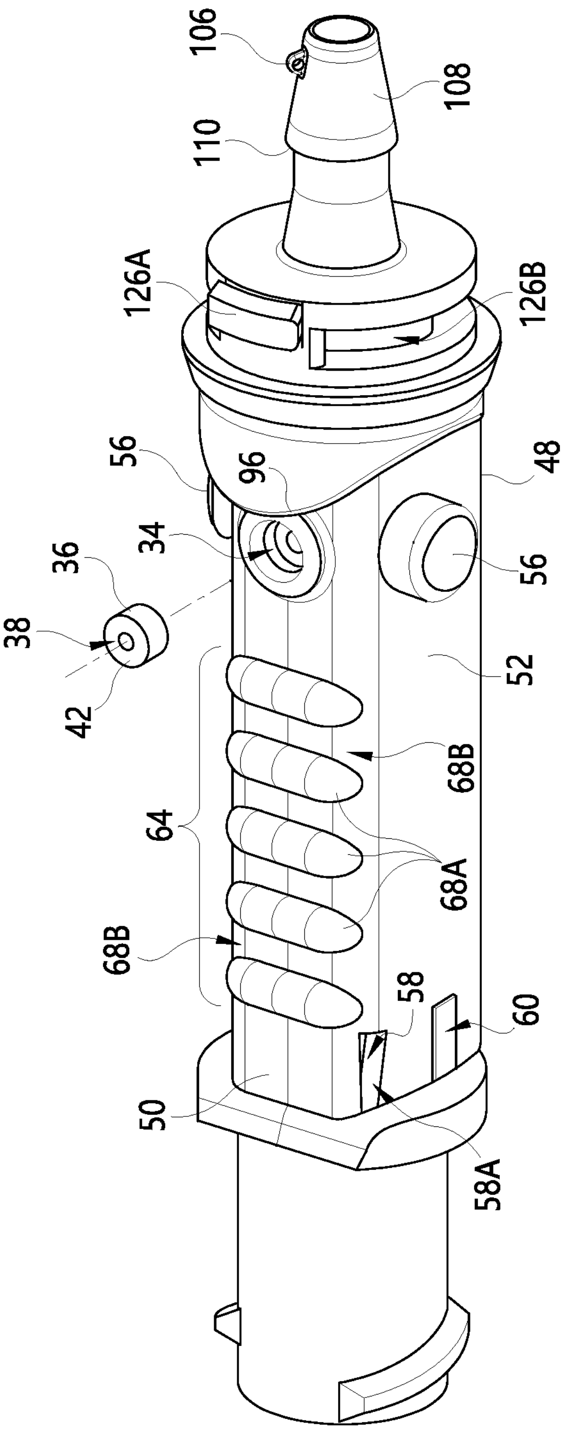
FIG. 2 provides a perspective view of the hub body of the catheter of FIG. 1.
Figure 3:
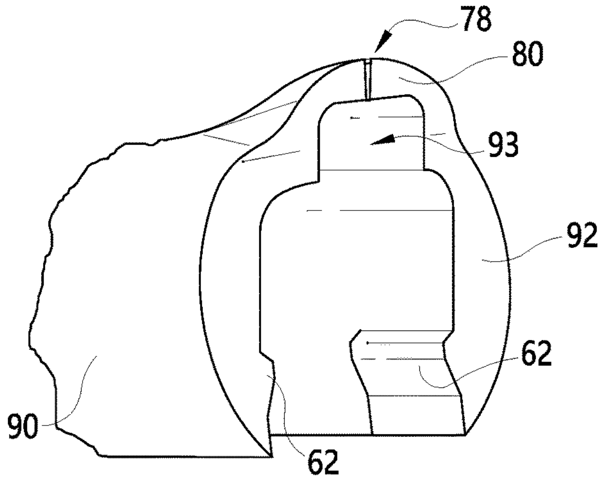
FIG. 3 provides a partial cutaway perspective view of the proximal end of the locking arm of the catheter of FIG. 1.
Figure 4:
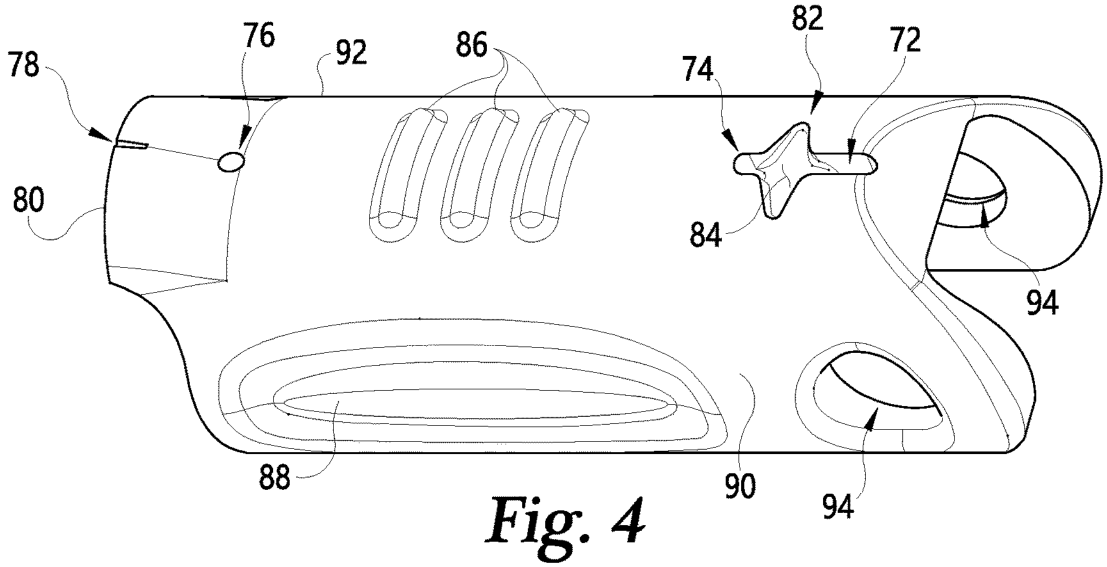
FIG. 4 provides a top perspective view of the locking arm of the catheter of FIG. 1 showing outer features thereof.
Figure 5:
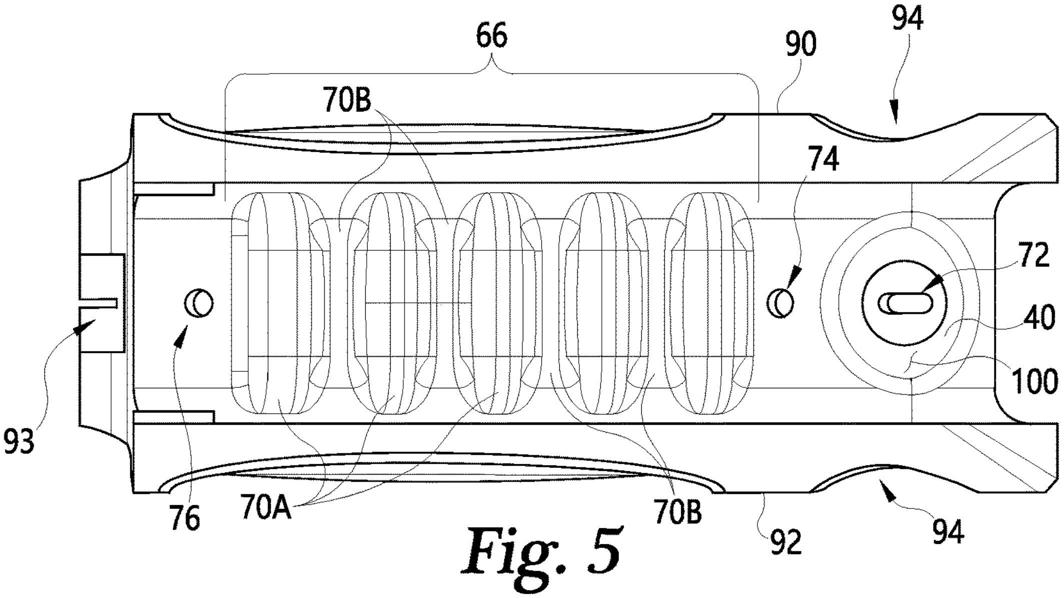
FIG. 5 provides a bottom view of the locking arm of the catheter of FIG. 1 showing inner features thereof.
Figure 6:
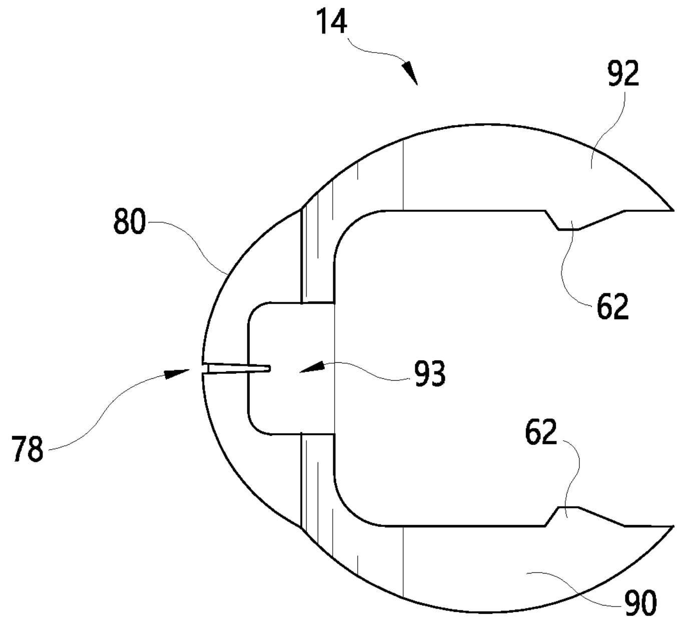
FIG. 6 provides a proximal end view of the locking arm of the catheter of FIG. 1.
Figure 9:
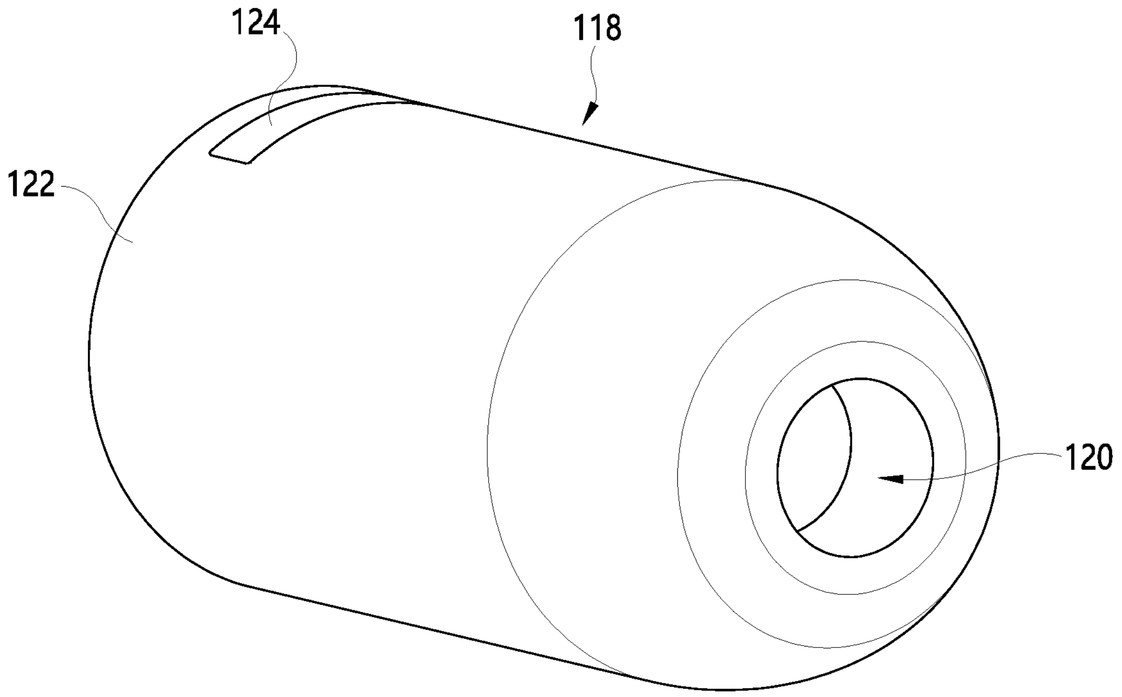
FIG. 9 provides a perspective view of the transitional cap of the catheter of FIG. 1.

In one aspect, the present disclosure provides a catheter including a catheter tube defining a catheter lumen, the catheter tube having a distal region. A hub is attached to the catheter tube and includes a hub body and a locking arm connected to the hub body. The locking arm has an outer surface defining a cutting notch that can have a cutting notch bottom wall. The catheter also includes a filament for securing the distal region of the catheter tube in an anchoring profile, the filament extending from the distal region of the catheter tube to the hub. The filament includes a proximal filament segment external of the hub body, and the proximal filament segment is positionable to a filament path providing a first filament portion extending over the cutting notch bottom wall of the locking arm outer surface and a second filament portion extending between the locking arm and the hub body. The locking arm is movable relative to the hub body between an unlocked position in which the second filament portion is not positionally fixed by compression between the locking arm and the hub body, and a locked position in which the second filament portion is positionally fixed by compression between the locking arm and the hub body for securing the distal region of the catheter tube in the anchoring profile. In some forms, the hub body defines a hub lumen in fluid communication with the catheter lumen and a seal seat passage fluidly communicating with the hub lumen and having a seal seat passage opening at a location on an outer surface of the hub body, and a sealing element is at least partially positioned in the seal seat passage. The filament can pass from the catheter lumen into the hub lumen, through the seal seat passage and sealing element, and out of the seal seat passage opening. The locking arm can have an inner surface facing the outer surface of the hub body, with the inner surface of the locking arm having a filament fixing region cooperable with a filament fixing region of the outer surface of the hub body to compress and thereby positionally fix the second filament portion when the locking arm is in the locked position. The filament fixing region of the outer surface of the hub body can include a protrusion or protrusions for cooperating with a recess or recesses of the filament fixing region of the inner surface of the locking arm, and/or the filament fixing region of the inner surface of the locking arm can include a protrusion or protrusions for cooperating with a recess or recesses of the filament fixing region of the outer surface of the hub body.

In another aspect, the present disclosure provides a method for securing and releasing a distal anchor of a catheter, the catheter including a hub, a catheter tube attached to the hub and having a distal region securable in an anchoring profile, and a filament extending from the distal region of the catheter tube to the hub, the filament having a first portion and a second portion. The method includes moving a locking arm of the hub to a locked position to compress the second portion of the filament between the locking arm and a hub body of the hub and thereby provide a secured condition of the distal region in the anchoring profile. The method also includes inserting a cutting edge into a cutting notch defined in an outer surface of the locking arm so as to cut the first portion of the filament positioned in the cutting notch, so as to release the secured condition of the distal region in the anchoring profile. The secured condition of the distal region in the anchoring profile can be held by a tensioned length of the filament, and the first portion can occur within the tensioned length of the filament. The cutting notch can have a bottom surface that is recessed relative to surfaces of the locking arm adjacent to the cutting notch.

In another aspect, the present disclosure provides a catheter including a catheter tube defining a catheter lumen, the catheter tube having a distal region. A hub is attached to the catheter tube, with the hub including a hub body and a locking arm connected to the hub body. The locking arm is movable relative to the hub body between an unlocked position for allowing travel of a filament portion between the locking arm and the hub body and a locked position in which the filament portion is positionally fixed by compression between a filament fixing region of the locking arm and a filament fixing region of the hub body for securing the distal region of the catheter tube in an anchoring profile. When the locking arm is in the locked position in a relaxed condition, at least a portion of the fixing region of the locking arm is spaced a distance from the fixing region of the hub body. Also included is a filament for securing the distal region of the catheter tube in an anchoring profile, the filament extending from the distal region of the catheter tube to the hub. The filament includes a proximal filament segment external of the hub body, wherein the proximal filament segment includes the filament portion, wherein the filament portion has a diameter, and wherein the ratio of said diameter to said distance is in the range of about 1.2:1 to about 3:1. The filament fixing region of the outer surface of the hub body can include a protrusion or protrusions for cooperating with a recess or recesses of the filament fixing region of the inner surface of the locking arm, and/or the filament fixing region of the inner surface of the locking arm can include a protrusion or protrusions for cooperating with a recess or recesses of the filament fixing region of the outer surface of the hub body. The locking arm can define a first opening and a second opening, and the proximal filament segment can extend in a filament path that exits the hub body and passes through the first opening to the outer surface of the locking arm, and through the second opening and into a compression zone between the fixing region of the inner surface of the locking arm and the fixing region of the outer surface of the hub body. The locking arm can also define a third opening, and the filament path can exit the compression zone and pass through the third opening to the outer surface of the locking arm. The locking arm can define a cinching notch proximal of the third opening, with the cinching notch configured to grip and secure the filament when forced into the notch.

In still another aspect, the present disclosure provides a method for securing a distal region of a catheter in an anchoring profile, the catheter including a hub, a catheter tube attached to the hub and having a distal region securable in the anchoring profile, and a filament extending from the distal region of the catheter tube to the hub. The method includes providing a portion of the filament positioned between a fixing surface of the locking arm and a fixing surface of the hub body, the portion of the filament having a diameter. The method further includes moving the locking arm to a locked position to compress the portion of the filament between the fixing surface of locking arm and the fixing surface of the hub body and thereby provide a secured condition of the distal region in the anchoring profile. In the method, the locking arm and hub body are configured such that when the locking arm is in the locked position in a relaxed condition, at least a portion of the fixing surface of the locking arm is spaced a distance from the fixing surface of the hub body, wherein the ratio of said diameter to said distance is in the range of about 1.2:1 to about 3:1.

Additional aspects of the present disclosure, including but not limited to methods of assembling catheters as disclosed herein, as well as features and advantages thereof, will be apparent to those skilled in the pertinent field from the disclosures herein.

DETAILED DESCRIPTION

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the claims is thereby intended. Any alterations and further modifications in the described embodiments and any further applications of the principles of the present disclosure as described herein are contemplated as would normally occur to one skilled in the art to which the disclosure relates.

As disclosed above, in certain aspects, the present disclosure provides catheter devices and methods of their preparation and use. The catheters can have a distal catheter tube region that can be secured in an anchoring profile by a locking engagement of a filament at a catheter hub. The catheter hub can include a locking arm that cooperates with a hub body to provide a locked position that compresses and positionally fixes a first portion of the filament between a fixing surface of the locking arm and a fixing surface of the hub body. The locking arm can define a cutting notch in its outer surface through which a second portion of the filament passes in the locked position, and the second portion of the filament can be cut to release the secured condition of the anchoring profile as the locked position of the hub is maintained. The locked position defined between the hub body and the locking arm can leave at least a portion of the respective fixing surfaces of the locking arm and the hub body spaced from one another a distance, when in a relaxed or unstressed condition. The locking arm can include first, second and third holes for routing the filament between the inner and outer surfaces of the locking arm, which can provide a filament path extending through the cutting notch and between the fixing surfaces of the locking arm and hub body. The locking arm can define a cinching notch for cinching (gripping by friction) and thereby securing a proximal-most segment of the filament when a segment of the filament is forced into the notch. At least a portion of the cinching notch can have a width that is less than the diameter of the forced segment of the filament for these purposes. These and other features of a catheter can be provided singly or in various combinations, including combinations with features provided in the Detailed Description below.

In discussions herein, the terms "proximal" and "distal" will be used to describe the opposing axial ends of the catheter, as well as the opposing axial ends of component features, such as the drainage catheter hub. The term "proximal" is used in its conventional sense to refer to the end of the catheter, or component feature, that is closest to the operator during use. The term "distal" is used in its conventional sense to refer to the end of the catheter, or component feature, that is furthest from the operator during use.

With reference now to FIGS. 1 through 9, there is shown a drainage catheter 200 and components thereof according to one embodiment of the present disclosure. In this illustrative arrangement, the catheter 200 has a hub 10 that includes a hub body 12 and a locking arm 14 attached and movable with respect to the hub body 12. The locking arm 14 is movable to a locked position to compress a filament 16 between the locking arm 14 and hub body 12 to fix the position of the compressed portion of the filament 16. The hub body has a distal end 18 that is configured to engage with a catheter tube 20 at a proximal end 22 of the tube 20. The hub body 12 also includes a connector end 24 (e.g. a tapered or threaded luer lock end) that is configured for attachment to a drainage collection system (not shown). The hub body 12 defines a hub lumen 26 that fluidly communicates with a catheter lumen 28 of the catheter tube 20. The hub body also defines a seal seat passage 30 that fluidly communicates with the hub lumen 26, with the passage 30 having a first passage opening 32 (see FIGS. 7 and 8) at the hub lumen 26 and a second passage opening 34 (FIG. 2) at a location on the external surface of the hub body 12. A sealing element 36 is received in the seal seat passage 30. In its relaxed state, sealing element 36 defines a seal element lumen 38 extending through the seal element 36, through which the filament 16 passes. As received in the seal seat passage 30, the sealing element 36 is radially compressed to close the seal element lumen 38 around the portion of the filament 16 passing through the seal element 36. In some embodiments, an inner surface portion 40 of the locking arm 14 is configured to contact, and optionally press against and compress, an upper surface 42 of the sealing element 36 when the locking arm 14 is in a locked position relative to the hub body 12. A configuration where the inner surface portion 40 presses against upper surface 42 can cause compression of the sealing element 36 to enhance the seal of the sealing element 36 against the filament 16.

The particular illustrated hub body 12 extends along a longitudinal axis in a substantially cylindrical fashion between its distal end 44 and its proximal end 46. The hub lumen 26 extends longitudinally between the distal end 44 and the proximal end 46. The hub lumen 26 is configured to receive a portion of the filament 16 and enable liquids and/or gases to pass therethrough.

The hub body 12 includes a lower body portion 48 opposite an upper body portion 50 and a right face 52 opposite a left face 54 wherein the lower and upper portions 48 and 50 and the right and left faces 52 and 54 occur between the distal and the proximal ends 44 and 46. Generally, the lower body portion 48 has a substantially smooth outer surface. Each of the right and left faces 52 and 54, respectively, includes a post 56 positioned closer to the distal end 46 of the hub body 12. In one form, the posts 56 have a cylindrical shape and extend a distance outward from the right and left faces 52 and 54, respectively. The posts 56 are sized and configured to engage and retain the locking arm 14 such that the locking arm 14 is able to rotate about the posts 56 to provide a pivotal connection of the locking arm 14 to the hub body 12. It will be understood that other movable connections are also contemplated as within the scope of this disclosure. Each of the right and left faces 52 and 54 also includes a transition recess 58 spaced a distance from a locking recess 60, wherein the transition recess 58 and the locking recess 60 are positioned closer to the proximal end 46 than the distal end 44. The transition and locking recesses 58 and 60 are sized and configured to cooperate with an interior nub 62 on each side of the locking arm 14, where when moving the locking arm 14 toward its locked position the nubs 62 enter transition recesses 58 and a user receives a tactile indication of cooperation between the locking arm 14 and the hub body 12, in the form of resistance to further travel. That resistance can be overcome with force applied to the locking arm 14 to outwardly flex the locking arm side portions 90 and 92 defining the nubs 62, whereupon the nubs 62 travel further toward locking recesses 60 and then enter locking recesses 60 with inward flexure of the locking arm side portions 90 and 92, to establish the locking arm 14 in its locked position relative to the hub body 12. The transition recesses 58 each provide a ramp surface 58A that slopes outwardly in a direction extending toward the lower body portion 48, which can facilitate the engagement and downward slide of the nubs 62 onto the right and left faces 52 and 54, respectively, prior to the entry of the nubs 62 into the locking recesses 60 to provide the locked position of the hub 10. In some embodiments, such a locked position spaces at least a portion of filament fixing surface regions from one another, as discussed herein.

The upper body portion 50 of the hub 12 defines the seal seat passage 30 that spans from the hub lumen 26 to the external surface of the hub body 12. The passage 30 is sized to receive and retain the sealing element 36. The passage 30 can be generally cylindrical in shape, although other shapes are also contemplated as suitable for use herein. In some forms, the passage 30 has an inner diameter that is smaller than the outer diameter of the sealing element 36, so that insertion of the sealing element 36 into the passage 30 causes inward radial compression of the sealing element 36. This can in turn deform the sealing element 36 to enhance the seal between the sealing element 36 and the portion of the filament 16 passing therethrough.

The upper body portion 50 defines an outer surface that includes a filament fixing region 64 and the locking arm defines an inner surface that includes a filament fixing region 66. Surface regions 64 and 66 cooperate to form a compression zone for compressing a portion of the filament 16. When the locking arm 14 is in a locked position relative to the hub body 12, the fixing region 64 and the fixing region 66 compress and thereby positionally fix the portion of the filament 16 positioned between the fixing regions 64 and 66. In beneficial forms, the filament fixing region 64 includes at least one protrusion for cooperating with a recess of the filament fixing region 66, and/or the filament fixing region 66 includes at least one protrusion for cooperating with a recess of the filament fixing region 64. In certain forms, the filament fixing region 64 includes a plurality of protrusions for cooperating with a plurality of recesses of the filament fixing region 66, and/or the filament fixing region 66 includes a plurality of protrusions for cooperating with a plurality of recesses of the filament fixing region 64. The protrusion(s) can have any suitable contour, for example having a polygonal shape (e.g. a triangular or rectangular shape) or a curved shape presenting a smoothly rounded convex surface contour, and in beneficial forms are elongate in a direction transverse to the longitudinal axis of the hub body 12 and locking arm 14 (e.g. in the form of elongate rib protrusion(s)). The recess(es) for cooperating with the protrusion(s) can present a concave surface contour that may correspond to the contour of the protrusion(s), for example a triangular recess(es) for cooperating with a triangular protrusion(s), a rectangular recess(es) for cooperating with a rectangular protrusion(s), or a curved recess(es) for cooperating with a curved protrusion(s). In other embodiments, the recess(es) can present a concave surface contour that does not correspond to the contour of the protrusion(s) with which it or they cooperate. The recess(es) in beneficial forms are also elongate in a direction transverse to the longitudinal axis of the hub body 12 and locking arm 14, for example in the form of elongate troughs. In the illustrated embodiment, provided on the hub body 12 are a plurality of curved protrusions 68A, each defining an elongate, smoothly-curved apex surface contour, and provided on the locking arm 14 are a plurality of recesses 70A, each defining a concave contour that does not correspond to the contour of their respective opposed protrusions 68A, and thus does not extend in parallel to the surface contour of the opposed protrusions 68A in the locked position. As well, provided on the locking arm 14 are a plurality of curved protrusions 70B, each defining an elongate, smoothly-curved apex surface contour, and provided on the hub body 12 are a plurality of recesses 68B, each defining a concave contour that does not correspond to the contour of their respective opposed protrusions 70B, and thus does not extend in parallel to the surface contour of the opposed protrusions 70B in the locked position. It will be understood that in other embodiments, recess(es) on the hub body 12 and/or locking arm 14 can define a surface contour that extends in parallel to the surface contour of their opposed protrusion(s) in the locked position of the locking arm 14.

Figure 7:
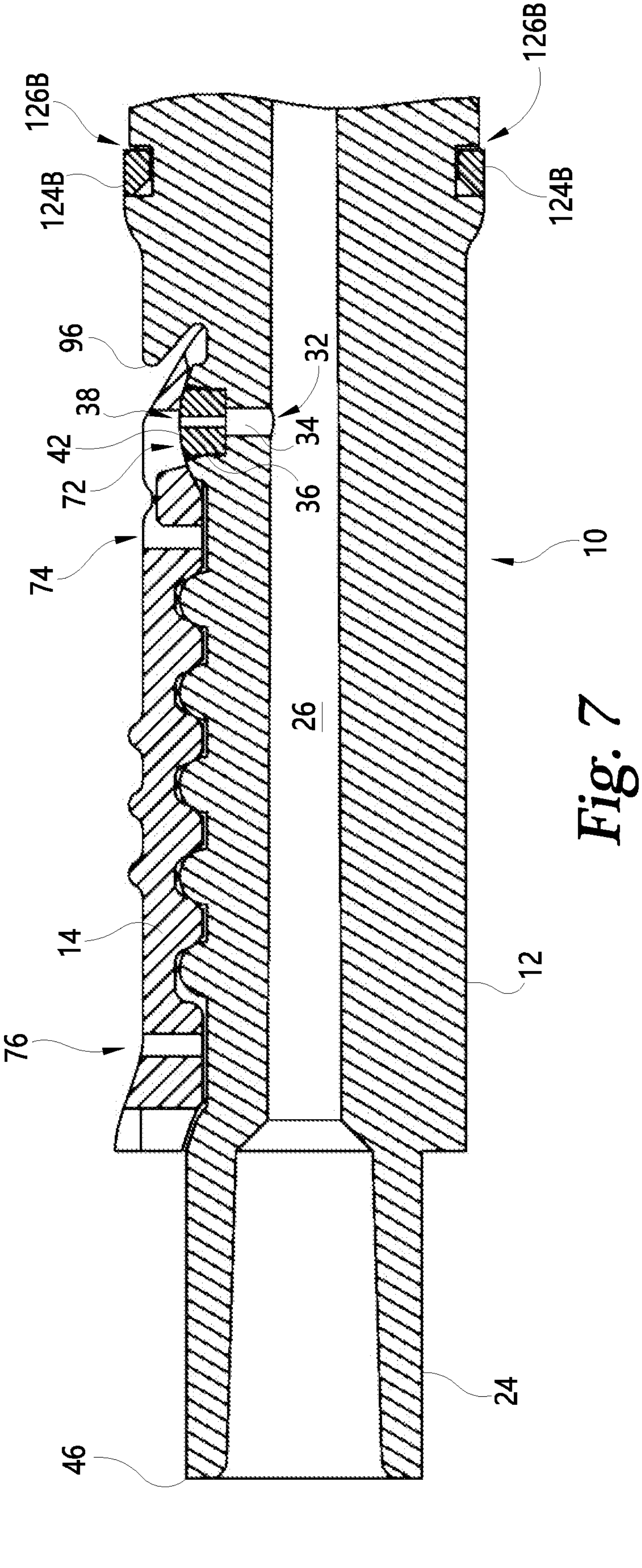
FIG. 7 provides a partial cutaway cross-sectional view of the assembled hub body and locking arm of the catheter of FIG. 1 in a locked position.

The locking arm 14 is movable relative to the hub body 12 between an unlocked position (see e.g. FIG. 8) and a locked position (see e.g. FIGS. 1 and 7). In the unlocked position, a portion of filament 16 located between fixing region 64 and fixing region 66 is not positionally fixed and can slide longitudinally. In the locked position, a portion of filament 16 located between fixing region 64 and fixing region 66 is compressed between regions 64 and 66 and thereby positionally fixed so as to secure a distal region of the catheter tube in an anchoring profile, for example a profile as discussed further below. In certain embodiments, when the locking arm 14 is in the locked position relative to the hub body 12 and in a relaxed (unstressed) condition, at least a portion of, or at least a plurality of portions of, the fixing region 66 of the locking arm 14 is/are spaced a distance "D" (see FIG. 1) from the fixing region 64 of the hub body 12. In preferred forms, a portion of the filament 16 to be received and compressed between fixing surfaces 64 and 66 has an outer diameter, and the distance D is selected to define a ratio relative to such outer diameter of at about 1.2:1 or greater, for example in the range of about 1.2:1 to about 3:1, or in the range of about 1.5:1 to about 2:1. With a defined spacing between fixing regions 64 and 66 in the locked position, it has been discovered that a more facile and reliable movement of the locking arm 14 to its locked condition relative to hub body 12 can be facilitated, e.g. as compared to a configuration in which the fixing regions 64 and 66 are configured continuously contact one another when the locking arm 14 is in the locked position relative to the hub body 12 in a relaxed condition (without a filament received between the arm 14 and body 12). In advantageous forms, a substantial percentage (i.e. greater than about 20%) of the surface area of the fixing region 64 is spaced the distance D from the fixing region 66 with the locking arm 14 in the locked position in a relaxed condition, more preferably greater than about 50%, and in some forms in the range of about 80% to about 100%.

The locking arm 14 includes features for defining a filament management path in association with the hub 10. In the illustrated embodiment, the locking arm 14 defines a first opening 72 that is sized to receive the filament 16 therethrough in a direction from the inner surface of the locking arm 14 to the external surface of the locking arm 14. The first opening 72 is desirably positionable to longitudinally coincide at least in part with and in some forms entirely with the seal seat passage opening 34, for example when the locking arm 14 is in the locked position, and/or is desirably elongate in the longitudinal direction of the hub 10. The locking arm also defines a second opening 74 spaced proximally from the first opening 72 and sized to receive the filament 16 therethrough in a direction from the outer surface to the inner surface of the locking arm 14. The locking arm 14 also defines a third opening 76 at a position spaced proximally from the second opening and sized to receive the filament 16 therethrough in a direction from the inner surface to the outer surface of the locking arm 14. The second opening 74 and the third opening 76 occur to either side of the fixing region 66 of the locking arm 14. In this manner, a proximal segment of the filament that is external of the hub body 12 can be positioned in a filament path that passes through the first opening 72 to the external surface of the locking arm 14, over the external surface of the locking arm to the second opening 74, through the second opening 74 to the internal surface of the locking arm, across the fixing surface 70 of the locking arm 14, to the third opening 76, and through the third opening 76 to the external surface of the locking arm 14 (see FIG. 1). A proximal-most length of the filament 16 can then be exposed out of the third opening 76. In certain forms, the locking arm 14 further defines a cinching notch 78, desirably at or proximate to the proximal end 80 of the locking arm 14. The proximal-most length of the filament 16 can be cinched and secured in the cinching notch 78 and, if desired, an end portion of the filament 16 extending proximally beyond the notch 78 can be trimmed off.

All or some of the transitions between surfaces in the filament management path, including surfaces on the hub body 12 and on the locking arm 14, can be filleted. In this manner, smooth or smoother travel of the filament longitudinally through the filament path can be provided. Thus, the transition between the surface of the hub lumen 26 and the inner wall of seal seat passage can be filleted; and/or the transition between the wall of the opening 72 and the bottom wall 84 of the notch 82 can be filleted; and/or the transition between the bottom wall 84 of the cutting notch 82 and the wall of the opening 74 can be filleted; and/or the transition between the wall of the opening 74 and the filament fixing surface region 66 can be filleted; and/or the transition between the filament fixing surface region 66 and the wall of the opening 76 can be filleted; and/or the transition between the wall of the opening 76 and the adjacent outer surface of the locking arm 14 can be filleted. In some embodiments, each of these surface transitions can be filleted. A filleted transition between two surfaces provides a smooth rounded corner between the two surfaces, which in some forms may be a constant-radius rounded surface.

In the illustrated embodiment, the locking arm 14 defines an elongate cutting notch 82 positioned between the first opening 72 and the second opening 74. The cutting notch 82 can be elongate in a direction transverse (e.g. perpendicular) to the path of filament 16 between the first and second openings 72 and 74, which can also be transverse (e.g. perpendicular) to the longitudinal axis of the hub 10. Cutting notch 82 has a bottom surface 84 defined by the locking arm 14 and occurring as a portion of the external surface of the locking arm 14. In use, the portion of filament 16 passing through cutting notch 14 can be severed, for example by inserting a sharp edge of an instrument (e.g. a scalpel) into the cutting notch 82, to release the secured condition of the distal region 102 of the catheter tube 20 in the anchoring profile. This can be done while the locking arm 14 is in its locked position relative to the hub body 12. In advantageous forms, as in the illustrated form, the bottom surface 84 of the cutting notch 82 is recessed relative to the outer surfaces of the locking arm adjacent to the cutting notch 82, so that a portion of the filament 16 passing over and against bottom surface 84 is also recessed relative to such adjacent outer surfaces. In this manner, the portion of the filament passing through cutting notch 82 can be relatively protected against undesired contact, for instance snagging or rubbing, during use of catheter 200 with the locking arm 14 in the locked position (e.g. during the catheter 200 insertion procedure or during an indwelling period of catheter 200).

As to other features, the locking arm 14 can also include at least one, or a plurality of, top rib(s) 86 defined on its exterior surface. The locking arm 14 can also include one or more elongated side ribs 88 on its exterior surface along a right side portion 90 and along a left side portion 92 of the locking arm 14. The top rib(s) 86 and the side rib(s) 88 provide a tactile sensation to a user when they grip or handle the catheter hub 10. The top and side rib(s) 86 and 88 can also provide a gripping surface for a user such that when a syringe is secured to the catheter hub 10, the user has a gripping surface to hold onto to prevent the catheter hub 10 from rotating. The locking arm 14 can also include an undercut recess 93 at or proximate to the proximal end 80. The tip of an implement such as a pair of forceps can be used to engage undercut recess 93 and pry upon locking arm 14 to forcibly release it from its locked position relative to hub body 12, during which nubs 62 will be forced to exit locking recesses 60 and arm 14 will pivot away from hub body 12.

The locking arm 14 in the illustrated embodiment it defines a concave interior shape configured to enclose and substantially cover the upper body portion 50, the right face 52, and the left face 54 of the hub body 12. Each of the right side portion 90 and left side portion 92 of the locking arm 14 defines an opening 94 that is sized and positioned to receive the corresponding post 56 therein to attach the locking arm 14 to the hub body 12. In assembling the locking arm 14 onto the hub body 12, the right and left side portions 90 and 92 of the locking arm 14 can be flexed outwardly to position the openings 94 over the posts 56, and then caused or allowed to flex back inwardly to position and retain the posts 56 within the openings 94. Other cooperative connections of the locking arm 14 and hub body 12 are contemplated. For example, in one alternative, the hub body 12 may define a hole and the locking arm 14 may include a post receivable in the hole to connect the locking arm 14 to the hub body 12. Other embodiments may include still other cooperative connections between the locking arm 14 and the hub body 12 that permit movement of the two relative to one another, and may include for example pivoting connections, hinged connections, sliding connections or other movable connections.

With the locking arm 14 connected to the hub body 12, the locking arm 14 can rotate to the locked position as discussed above. Rotation in the opposite (opening) direction is also permitted, preferably to a stop point at which an interaction between a locking arm 14 surface and a hub body 12 surface prevents further rotation in the opening direction. In the illustrated embodiment, the hub body 12 defines a boss region 96 (see FIG. 8) that contacts a distal stop region 98 of the outer surface of the locking arm 14 to prevent further rotation of the locking arm 14 in the opening direction. As illustrated, the boss region 96 can occur on a proximally-facing ridge defined by the hub body 12 that longitudinally overlaps a portion of the outer surface of the locking arm 14 and contacts the stop region 98 thereof at the stop point. In some forms, with the locked position of the locking arm 14 considered as 0 degrees, the locking arm can be rotated to a stop point in the range of about 5 degrees to about 50 degrees, or in some forms in the range of about 10 degrees to about 30 degrees.

As discussed above, in certain embodiments, when in the locked position relative to the hub body 12, the locking arm 14 can contact, and in certain variants compress, the sealing element 36. When the locking arm 14 compresses the sealing element 36, this compression can enhance a seal around the filament 16 by the sealing element 36, while still allowing longitudinal movement of the filament 16 through the sealing element 36 (when the locking arm is in an unlocked position). For these purposes, the interior surface of the locking arm 14 can include a seal-engagement portion 40. In the illustrated embodiment, the engagement portion 40 is movable out of contact with the sealing element 36 by rotating the locking arm 14 in the opening direction. In certain forms, the engagement portion 40 can be circular in shape and can form a concave domed recess surface 100, as illustrated. Other embodiments of the engagement portion 100 can have different shapes or contours as appropriate to contact and in some forms compress a particular sealing element design or position in or on the hub. When the surface of the seal engagement portion 40 compresses the sealing element 36, it can cause the upper surface 42 of the sealing element 36 to conform to the shape of the surface of the seal-engagement portion 40, for example with the upper surface 42 being compressed to a domed convex shape conforming to the concave domed recess surface 100 in the illustrated embodiment, see e.g. FIG. 7.

The catheter tube 20 has a distal region 102 that is securable in an anchoring profile (FIG. 1). The anchoring profile can include a curved configuration of the distal region 102, including for example a coiled or "pigtail" configuration. In desirable forms, the distal region 102 is formed having shape memory that positions distal region 102 at least partially into its anchoring profile to be secured by tensioning filament 16, which extends from distal region 102 to the hub 10 in the illustrated embodiment passing through the lumen 28 of the catheter tube 20. As shown, the filament can include a first end region 104 secured to a distal location on the hub body 12. In one form, the hub body 12 includes a loop structure 106 (FIG. 2) on the external surface of a frusto-conical connection barb 108, distal to a proximal end 110 of the connection barb 108 providing the largest diameter of the barb 108. The loop structure 106 is desirably contained within the longitudinal profile defined by the proximal end 110 of the barb 108, with the outermost surface of the loop structure 106 extending radially outward from the central axis of the hub body 12 a distance equal to, or preferably less than, the distance that the proximal end 110 of the barb 108 extends radially outward from the central axis of the hub body 12. The first end region 104 of the filament 16 can extend through the opening of the loop structure 106 and be tied to the loop structure 106. The filament 16 can extend in a path distally from the end region 104 through the lumen 28 to the distal region 102 to exit a first opening 112. From first opening 112, the filament 16 travels external of the catheter tube 20 to a second opening 114 at a location distal to the first opening 112 along the length of catheter tube 20. Distal region can have additional openings 116 intermediate to the first and second openings 114 along the length of catheter tube 20. Filament 16 enters the second opening 114 and travels proximally in the catheter lumen 28 and into the hub lumen 26. Filament then extends through the seal seat passage 30 and the seal element 36, exiting the hub body 12 to provide an externalized proximal filament segment to be managed in a path by the features of the hub body 12 and locking arm 14, as discussed above.

The catheter 200 can also include a cap 118 (see FIG. 9 and cap shown in phantom in FIG. 1) that covers a transition region between the hub body 12 and the catheter tube 20 and can provide strain relief between the body 12 and tube 20. Cap 118 includes an end opening 120 through which catheter tube 20 is received, and a proximal connection region 122 for establishing a connection to the hub body 12. In the illustrated embodiment, the connection region 122 includes circumferentially-extending slots 124A and interiorly-directed posts 124B. The slots 124A can receive corresponding projections 126A on a distal region of hub body 12, and the posts 124B can be received in corresponding recesses

126B on the distal region of hub body 12, whereafter the cap 118 and hub body 12 can be rotated relative to one another to lock the cap 118 to the hub body 12.

Figure 10:
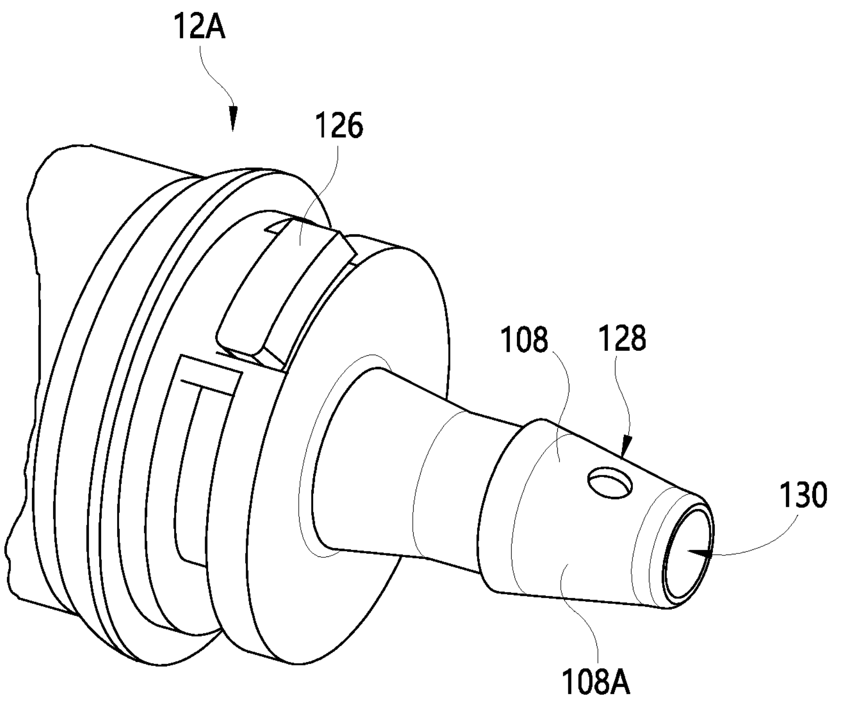
FIG. 10 provides a cutaway perspective view of the distal end region of an alternative hub body embodiment having an alternative filament end securing feature.
Figure 11:
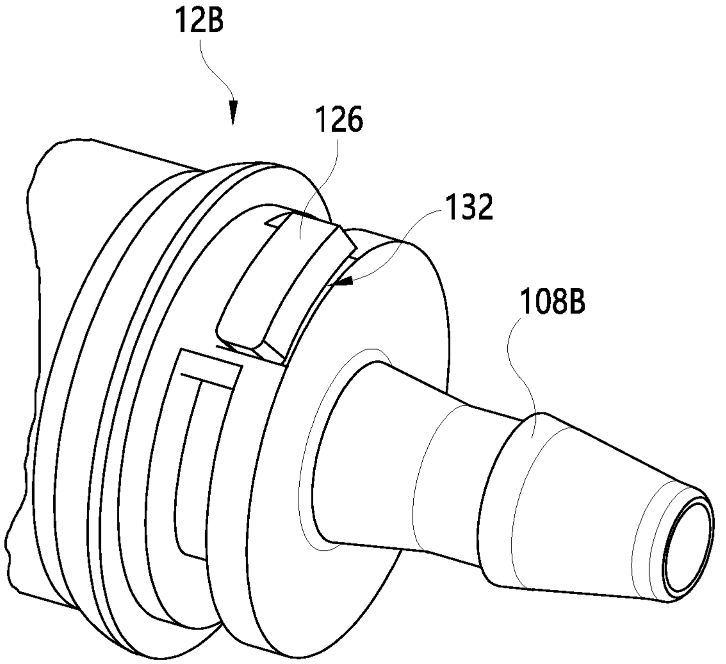
FIG. 11 provides a cutaway perspective view of the distal end region of another alternative hub body embodiment having an alternative filament end securing feature.

FIGS. 10 and 11 show hub body designs providing alternative features for securing the first end region 104 of the filament 16 to the hub body. Except for the following differences, the hub body 12A (FIG. 10) and the hub body 12B (FIG. 11) can have the same features as the hub body 12 discussed above. With reference to FIG. 10, the frusto-conical barb 108A in hub body 12A does not have the loop structure 106, but instead has a wall portion 126 that defines a thru-hole 128. The first end region 104 of filament 16 can be passed into the distal opening 130 and then through the thru-hole 128, and then tied to itself at that location. In this embodiment, like with hub body 12 discussed above, the first end region 104 of the filament 16 is attached to the hub body at a location distal of the largest-diameter proximal end of the barb 108A. This can provide an advantageous filament attachment in these specific illustrated embodiments or other embodiments within the present disclosure. With reference to FIG. 11, the frusto-conical barb 108B in hub body 12B does not have the loop structure 106, but instead the distal region of hub body for connecting the transition cap has a post that defines a post undercut region 132 around which the first end region 104 of the filament 16 can be tied to itself.

Illustrative methods of using the catheter 200 will now be described. Initially, the distal region 102 of the catheter tube 20 is percutaneously inserted into a body cavity, such as the bladder. This step can be performed by inserting the distal end of a thin-walled hollow needle through the abdominal wall and into the bladder in a well-known manner. A wire guide can then be inserted through the needle into the bladder, and the needle can be removed, leaving the wire guide in place. A dilator may be used alone or in conjunction with an introducer or access sheath over the wire guide to increase the size of the puncture site. In advantageous forms, the hub 10 defines a small enough outer profile so that it may be used with a 30 French sheath without deformation to the sheath.

Figure 8:
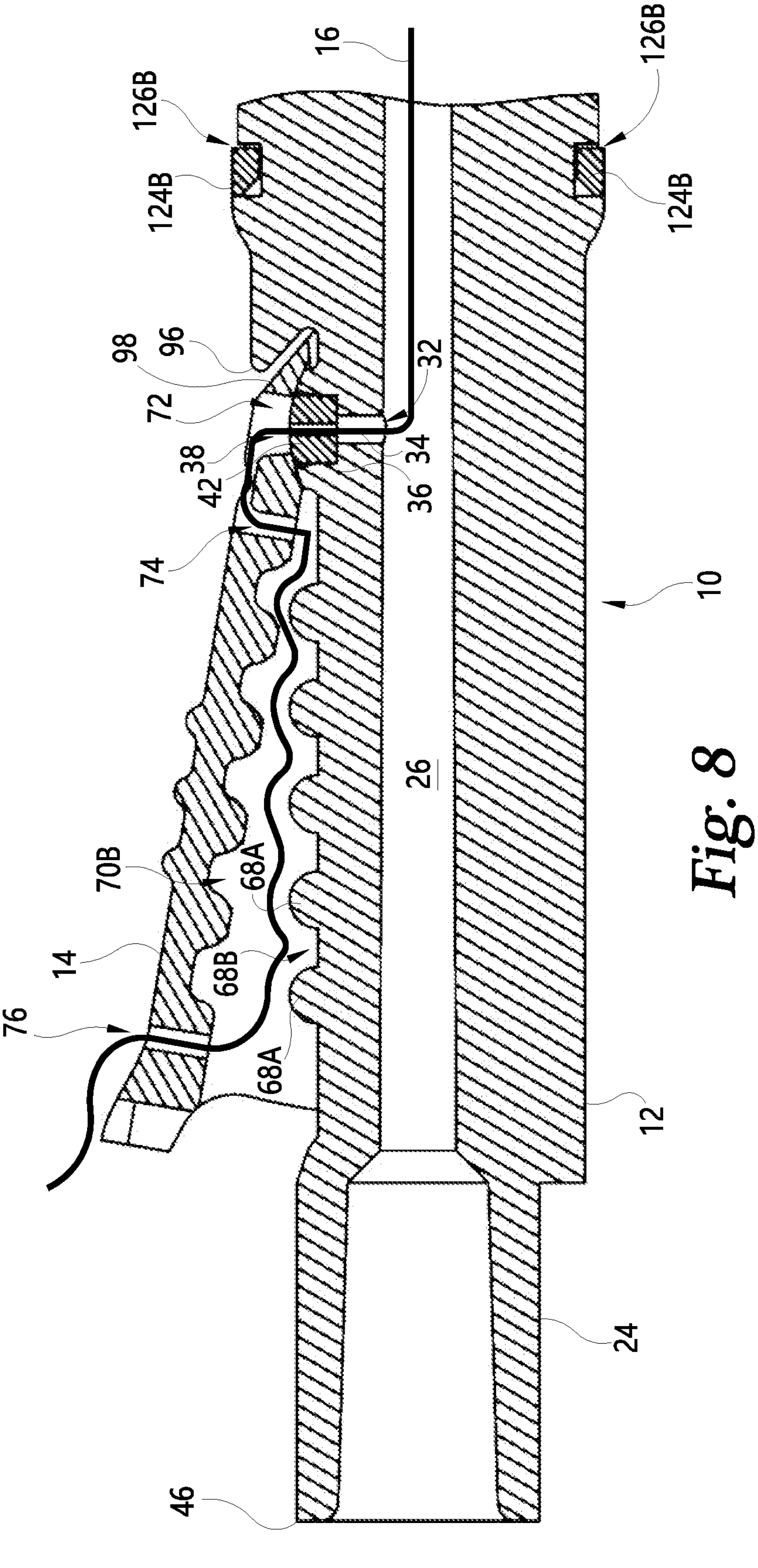
FIG. 8 provides a partial cutaway cross-sectional view of the assembled hub body and locking arm of the catheter of FIG. 1 in an unlocked or open position.

During percutaneous insertion of the catheter tube 20 over the wire guide, the catheter tube 20 will typically be manipulated into a generally straight configuration, with the locking arm 14 in an open position (e.g. as shown in FIG. 8). This generally straight configuration may be achieved by inserting a flexible stiffener (not shown), such as a stylet, through the hub lumen 26 and the catheter lumen 28. Following insertion of the straightened distal region 102 of the catheter tube 20 into the bladder, the wire guide and flexible stiffener can be removed from the patient. Where the distal region 102 has shape memory to self-configure to or toward the anchoring profile, the removal of the flexible stiffener will allow the region 104 to do so. The distal region 102 of the catheter tube 20 can be left in place for providing fluid flow from the bladder through the openings 112-116 of the distal region 102, through the catheter tube lumen 28, through the hub lumen 26, and to a conventional fluid collection system (not shown), such a system including for example a tubing fluidly coupled to the end 24 of the hub body 12 and a plastic collection bag.

To inhibit unintended withdrawal or dislodgement of the distal region 102 of the catheter tube 20 from the bladder or other body cavity, the locking features of the hub 10 are used to secure the distal region 102 in the anchoring profile, for example a loop as shown in FIG. 1.

To secure the anchoring profile, an operator can grasp and apply tension to the proximal portion of the filament 16, while the locking arm 14 is in an unlocked, or open position (FIG. 8), and then the locking arm 14 can be moved to its locked position (FIGS. 7 and 1). In some forms, where the distal region 102 has shape memory to self-configure toward the desired anchoring profile, the application of tension to filament 16 with the locking arm 14 in an unlocked position will reconfigure the self-configured profile caused by the shape memory to the final desired anchoring profile. In other forms, the distal region 102 may lack shape memory to or toward the desired anchoring profile (e.g. be generally straight), and the application of tension to the filament 16 with the locking arm 14 in the unlocked position can configure the distal region 102 from a generally straight profile to the desired anchoring profile. Movement of the locking arm 14 to the locked position relative to the hub body while maintaining the applied tension to the filament 16 can then secure the distal region 102 in the desired anchoring profile. The proximal-most portion of the filament 16 can then be secured in the cinching notch 78 and, if desired, some or all of the remaining filament extending proximal of the notch 78 can be trimmed off. In other uses, the cinching notch 78 can be employed to cinch the filament 16 for temporary filament positioning adjustments (e.g. to adjust tension on the filament 16) prior to locking the locking arm 14.

When removal of the catheter 200 from the patient is desired, in one mode of use, an operator can insert a sharp edge of an implement into cutting notch 82 to thereby sever the filament 16 at that location. This separates a portion of the filament proximal thereof that remains compressed and positionally fixed between fixing regions 64 and 66 of the hub body and locking arm, respectively, from a portion of the filament that occurs distal of severed filament location that is now capable of longitudinal movement in a distal direction. In another mode of use, the locking arm 14 can be forced from the locked position to an unlocked position, to thereby eliminate the positionally-fixing compression of the filament 16 by the fixing regions 64 and 66 and allow longitudinal movement of the filament in the distal direction. For this operation, in the illustrated embodiment, the tip of an instrument, such as the tip of a pair of forceps, can be inserted into undercut recess 90 and used to pry the locking arm 14 from its locked position to an unlocked position. After severing the filament 16 in the cutting notch 82, or after movement of the locking arm 14 to an unlocked position, the catheter 200 can be pulled from the patient during which the distal region 102 can return to a generally straight condition for travel through patient tissues. In cases where the distal region 102 has shape memory for configuring to or toward the anchoring profile, contact with patient tissues can overcome the shape memory and force the distal region 102 to a generally straight condition. Alternatively, it would be possible to insert a straightening implement such as a stylet into the catheter 20 to bring it to a generally straight condition, and the implement and catheter 20 removed together.

The components of a catheter system may be formed with any suitable material. These include for example synthetic polymeric materials. For example, the hub body 12 may be formed from a synthetic polymeric material, for example polybutylene terephthalate; the locking arm 14 may be formed from a suitable synthetic polymeric material, for example high density polyethylene; the catheter tube 20 may be formed from a suitable synthetic polymeric material, for example a polyurethane polymer; the filament 16 may be formed from a natural or synthetic polymeric material or a metallic material, and in preferred forms is a monofilament structure and especially a polyamide polymer (e.g. nylon) monofilament; the cap 118 may be formed from a suitable synthetic polymeric material, for example high density polyethylene; and, the sealing element 36 may be formed from an elastomeric material, for example a synthetic polymeric elastomeric material such as silicone. The components of hub assembly 100, including the hub body 102, the locking arm 14, and the sealing element 36, may be manufactured by injection molding. In one embodiment, the locking arm 14 is configured to flex more than the hub body 102, and for these purposes can be made from a synthetic polymeric material that has a lower tensile modulus than that of which the hub body 12 is made. The filament 16 may be manufactured by extrusion, especially when formed from a synthetic polymeric material.

The uses of the terms "a" and "an" and "the" and similar references herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the products or methods defined by the claims.

While embodiments of the disclosure have been illustrated and described in detail in the drawings and foregoing description, the same is to be considered as illustrative and not restrictive in character, it being understood that only some embodiments have been shown and described and that all changes and modifications that come within the spirit of the disclosures herein are desired to be protected.

The invention claimed is:

1. A catheter, comprising:

a catheter tube defining a catheter lumen, the catheter tube having a distal region;

a hub attached to the catheter tube, the hub including a hub body and a locking arm connected to the hub body, the locking arm having an outer surface defining a cutting notch having a cutting notch bottom wall;

a filament for securing the distal region of the catheter tube in a secured anchoring profile, the filament extending from the distal region of the catheter tube to the hub, the filament including a proximal filament segment external of the hub body, wherein the proximal filament segment is positionable to a filament path providing a first filament portion extending over the cutting notch bottom wall of the locking arm outer surface and a second filament portion extending between the locking arm and the hub body;

the locking arm movable relative to the hub body between an unlocked position in which the second filament portion is not positionally fixed by compression between the locking arm and the hub body and a locked position in which the second filament portion is positionally fixed by compression between the locking arm and the hub body for securing the distal region of the catheter tube in the secured anchoring profile; and wherein cutting the first filament portion at the cutting notch when the locking arm is in the locked position releases the distal region of the catheter tube from the secured anchoring profile.

2. The catheter of claim 1, wherein:

the hub body defines a hub lumen in fluid communication with the catheter lumen and a seal seat passage fluidly communicating with the hub lumen and having a seal seat passage opening at a location on an outer surface of the hub body;

a sealing element is at least partially positioned in the seal seat passage; and the filament passes from the catheter lumen into the hub lumen, through the seal seat passage and sealing element, and out of the seal seat passage opening.

3. The catheter of claim 1, wherein the locking arm has an inner surface facing the outer surface of the hub body, with the inner surface of the locking arm having a filament fixing region cooperable with a filament fixing region of the outer surface of the hub body to compress and thereby positionally fix the second filament portion when the locking arm is in the locked position.

4. The catheter of claim 3, wherein the filament fixing region of the outer surface of the hub body includes a protrusion for cooperating with a recess of the filament fixing region of the inner surface of the locking arm and/or wherein the filament fixing region of the inner surface of the locking arm includes a protrusion for cooperating with a recess of the filament fixing region of the outer surface of the hub body.

5. The catheter of claim 1, wherein the filament has a third portion positioned at the distal region of the catheter tube, and wherein the first filament portion is between the second filament portion and the third filament portion along the filament.

6. The catheter of claim 5, wherein:

the locking arm has an inner surface facing an outer surface of the hub body, with the inner surface of the locking arm having a first filament fixing region cooperable with a second filament fixing region of the outer surface of the hub body to compress and thereby positionally fix the second filament portion when the locking arm is in the locked position; and the cutting notch is distal of the first filament fixing region and the second filament fixing region along a length of the hub.

7. The catheter of claim 3, wherein when the locking arm is in the locked position in a relaxed condition, at least a portion of the filament fixing region of the inner surface of the locking arm is spaced a distance from the filament fixing region of the outer surface of the hub body.

8. The catheter of claim 7, wherein the second filament portion has a diameter, and wherein the ratio of said diameter to said distance is in the range of about 1.2:1 to about 3:1.

9. The catheter of claim 1, wherein:

the locking arm defines an inner surface facing toward the hub body and the outer surface faces away from the hub body;

the locking arm defines a first opening extending from the inner surface to the outer surface and a second opening spaced from the first opening and extending from the inner surface to the outer surface; and the filament path exits the hub body and passes through the first opening to the outer surface of the locking arm, through the cutting notch, and through the second opening and into a compression zone between a first filament fixing region of the inner surface of the locking arm and a second filament fixing region of the outer surface of the hub body, wherein the first filament fixing region is cooperable with the second filament fixing region to compress and thereby positionally fix the second filament portion when the locking arm is in the locked position.

10. A catheter, comprising:

a catheter tube defining a catheter lumen, the catheter tube having a distal region;

a hub attached to the catheter tube, the hub including a hub body and a locking arm connected to the hub body;

the locking arm movable relative to the hub body between an unlocked position for allowing travel of a filament portion between the locking arm and the hub body and a locked position in which the filament portion is positionally fixed by compression between a filament fixing surface region of the locking arm and a filament fixing surface region of the hub body for securing the distal region of the catheter tube in an anchoring profile, wherein when the locking arm is in the locked position in a relaxed condition, at least a portion of the filament fixing surface region of the locking arm is spaced a distance from the filament fixing surface region of the hub body;

a filament for securing the distal region of the catheter tube in an anchoring profile, the filament extending from the distal region of the catheter tube to the hub, the filament including a proximal filament segment external of the hub body, wherein the proximal filament segment includes the filament portion, wherein the filament portion has a diameter, and wherein the ratio of said diameter to said distance is about 1.2:1 or greater.

11. The catheter of claim 10, wherein the ratio of said diameter to said distance is in the range of about 1.2:1 to about 3:1.

12. The catheter of claim 10, wherein:

the hub body defines a hub lumen in fluid communication with the catheter lumen and a seal seat passage fluidly communicating with the hub lumen and having a seal seat passage opening at a location on an outer surface of the hub body;

a seal element is at least partially positioned in the seal seat passage; and the filament passes from the catheter lumen into the hub lumen, through the seal seat passage and seal element, and out of the seal seat passage opening.

13. The catheter of claim 10, wherein the filament fixing surface region of the hub body includes a protrusion for cooperating with a recess of the filament fixing surface region of the locking arm and/or wherein the filament fixing surface region of the locking arm includes a protrusion for cooperating with a recess of the filament fixing surface region of the hub body.

14. The catheter of claim 10, wherein the filament fixing surface region of the hub body includes a plurality of protrusions for cooperating with a plurality of recesses of the filament fixing surface region of the locking arm.

15. The catheter of claim 10, wherein the filament fixing surface region of the locking arm includes a plurality of protrusions for cooperating with a plurality of recesses of the filament fixing surface region of the hub body.

16. The catheter of claim 14, wherein the protrusions of the filament fixing surface of the hub body each have an apex surface, and wherein the apex surfaces of the protrusions of the filament fixing surface of the hub body are spaced said distance from the filament fixing surface region of the locking arm when the locking arm is in the locked position.

17. The catheter of claim 15, wherein the protrusions of the filament fixing surface region of the locking arm each have an apex surface, and wherein the apex surfaces of the protrusions of the filament fixing surface of the locking arm are spaced said distance from the filament fixing surface region of the hub body when the locking arm is in the locked position.

18. The catheter claim 10, wherein:

the locking arm has an inner surface facing toward the hub body and an outer surface facing away from the hub body;

the locking arm defines a first opening extending from the inner surface to the outer surface and a second opening extending from the inner surface to the outer surface; and the proximal filament segment extends in a filament path that exits the hub body and passes through the first opening to the outer surface of the locking arm, through a cutting notch on the outer surface of the locking arm, and through the second opening and into a compression zone between a filament fixing surface region of the locking arm and a filament fixing surface region of the hub body.

19. The catheter of claim 18, wherein:

the cutting notch extends only partly through a thickness of the locking arm from the outer surface to the inner surface, wherein a portion of the outer surface of the locking arm provides a bottom surface of the cutting notch.

20. A catheter, comprising:

a catheter tube defining a catheter lumen, the catheter tube having a distal region;

a hub attached to the catheter tube, the hub including a hub body and a locking arm connected to the hub body, the locking arm defining a first opening and a second opening;

a filament for securing the distal region of the catheter tube in a secured anchoring profile, the filament extending from the distal region of the catheter tube to the hub, the filament including a proximal filament segment external of the hub body, wherein the proximal filament segment is positionable to a filament path that exits the hub body and passes through the first opening to an outer surface of the locking arm, through a cutting notch defined by the locking arm, and through the second opening and into a compression zone between a fixing region of the inner surface of the locking arm and a fixing region of the outer surface of the hub body;

the locking arm movable relative to the hub body between an unlocked position in which a portion of the filament in the compression zone is not positionally fixed by compression between the locking arm and the hub body and a locked position in which the portion of the filament is positionally fixed by compression between the fixing region of the inner surface of the locking arm and the fixing region of the outer surface of the hub body for securing the distal region of the catheter tube in the secured anchoring profile; and wherein cutting the first filament portion at the cutting notch when the locking arm is in the locked position releases the distal region of the catheter tube from the secured anchoring profile.

21. The catheter of claim 20, wherein:

the locking arm defines a third opening; and the filament path exits the compression zone and passes through the third opening to the outer surface of the locking arm.

22. The catheter of claim 20, wherein:

the locking arm has an inner surface facing toward the hub body and an outer surface facing away from the hub body;

the first opening extends from the inner surface to the outer surface;

the second opening extends from the inner surface to the outer surface; and the locking arm defines a cutting notch between the first opening and the second opening, and the filament path extends through the cutting notch.

23. The catheter of claim 20, wherein when the locking arm is in the locked position in a relaxed condition, at least a portion of the filament fixing region of the inner surface of the locking arm is spaced a distance from the filament fixing region of the outer surface of the hub body.

24. The catheter of claim 1, wherein:

the outer surface of the locking arm faces away from the hub body;

the locking arm has an inner surface facing toward the hub body;

the cutting notch extends only partly through a thickness of the locking arm from the outer surface to the inner surface, wherein a portion of the outer surface of the locking arm provides a bottom surface of the cutting notch; and the cutting notch is configured for insertion of a sharp edge of an instrument into the cutting notch to sever the first filament portion while the locking arm is in the locked position.

25. The catheter of claim 24, wherein:

the proximal filament segment is positioned or positionable in the filament path such that the first filament portion extends through the cutting notch under tension and is recessed relative to portions of the outer surface of the locking arm that are adjacent to the cutting notch.

26. The catheter of claim 20, wherein:

the outer surface of the locking arm faces away from the hub body;

the inner surface of the locking arm is opposite the outer surface of the locking arm and faces toward the hub body;

the first opening and the second opening each extend from the inner surface of the locking arm to the outer surface of the locking arm; and the cutting notch extends only partly through a thickness of the locking arm from the outer surface to the inner surface, wherein a portion of the outer surface of the locking arm provides a bottom surface of the cutting notch.

* * * * *